United States Patent [19]

Meiri et al.

[11] 4,207,872
[45] Jun. 17, 1980

[54] DEVICE AND METHOD FOR ADVANCING AN ENDOSCOPE THROUGH A BODY PASSAGE

[75] Inventors: Samuel Meiri; Casey Kot, both of Skokie; B. H. Gerald Rogers, Chicago; Max Epstein, Highland Park, all of Ill.

[73] Assignee: Northwestern University, Evanston, Ill.

[21] Appl. No.: 861,113

[22] Filed: Dec. 16, 1977

[51] Int. Cl.$^2$ .................. A61B 1/00; A61M 25/00
[52] U.S. Cl. ........................... 128/4; 128/348; 128/DIG. 9; 254/134.6
[58] Field of Search ................. 128/276, 4–8, 128/2 M, DIG. 9, 348, 349, 349 B, 349 BU, 344, 246; 254/134.6, 93 HP

[56] References Cited

U.S. PATENT DOCUMENTS

| | | | |
|---|---|---|---|
| 2,855,934 | 10/1958 | Daughaday, Jr. | 128/349 R |
| 3,224,734 | 12/1965 | Hill | 254/134.6 |
| 3,485,237 | 12/1969 | Bedford | 128/2 M |
| 3,503,399 | 3/1970 | Ettman et al. | 128/349 B |
| 3,635,223 | 1/1972 | Klieman | 128/348 |
| 3,665,928 | 5/1972 | Del Guercio | 128/DIG. 9 |
| 3,811,448 | 5/1974 | Morton | 128/349 B |
| 3,895,637 | 7/1975 | Choy | 128/2 M X |
| 4,066,070 | 1/1978 | Otsugi | 128/4 |

FOREIGN PATENT DOCUMENTS

| | | | |
|---|---|---|---|
| 1170586 | 5/1964 | Fed. Rep. of Germany | 128/2 M |
| 2603684 | 8/1977 | Fed. Rep. of Germany | 128/DIG. 9 |
| 1278965 | 11/1961 | France | 128/349 R |

Primary Examiner—Paul T. Sewell
Assistant Examiner—Steven A. Bratlie
Attorney, Agent, or Firm—Tilton, Fallon, Lungmus & Chestnut

[57] ABSTRACT

A device and its method of operation for assisting in the advancement of an endoscope through the colon or other body passage. The device includes a sleeve having an annular chamber defined in part by an outer wall of resilient elastomeric material. A multiplicity of resilient hollow protrusions are formed in the wall and expand outwardly and rearwardly when the chamber is filled with a suitable fluid under pressure and which retract inwardly and forwardly when the pressure of the fluid is reduced. The device extends about and is secured to the distal end portion of an endoscope and, upon repetitious expansion and retraction of the protrusions by reason of pulsing pressure fluctuations within the chamber, such device helps to advance the scope along a body passage.

25 Claims, 6 Drawing Figures

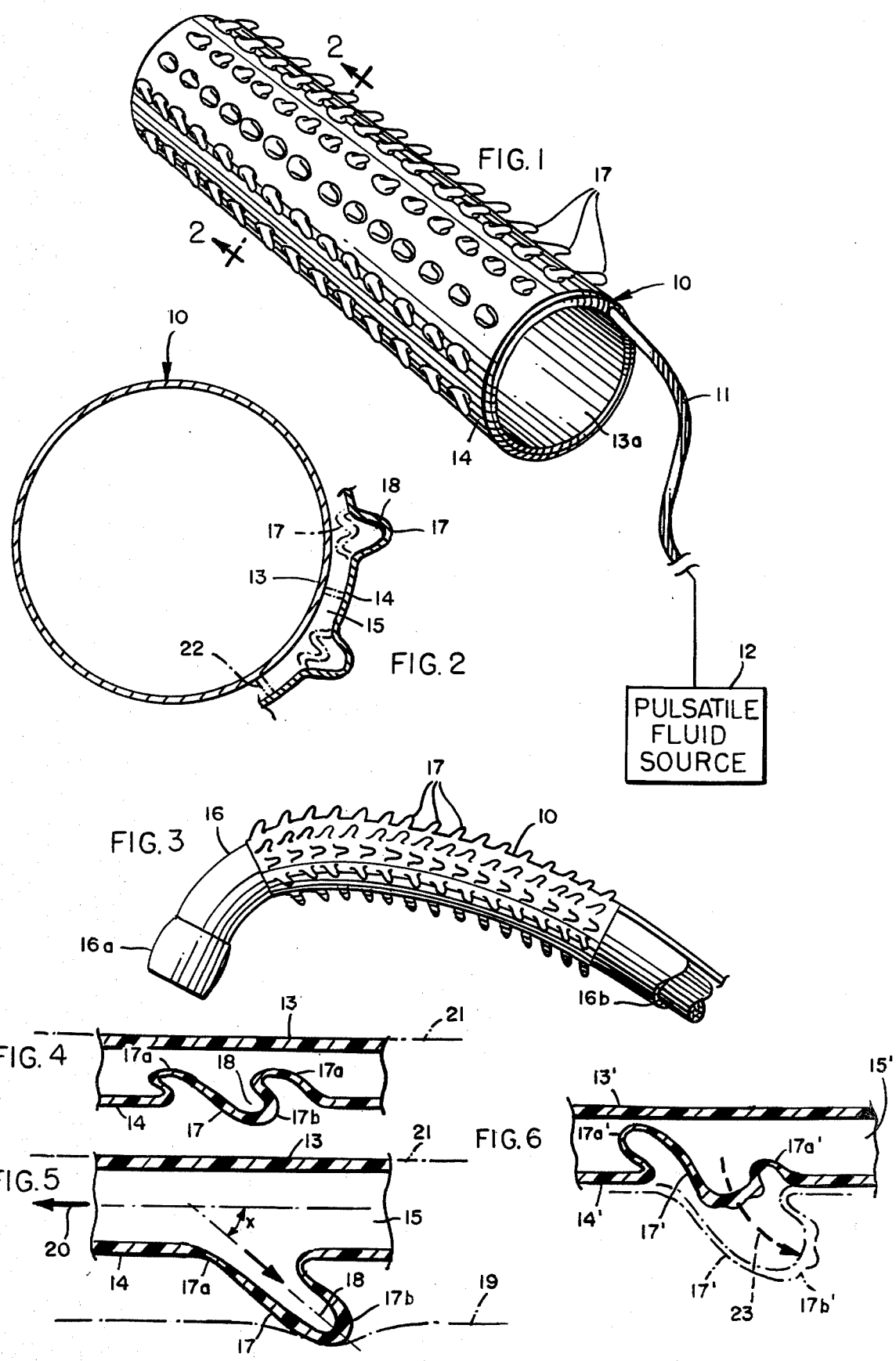

DEVICE AND METHOD FOR ADVANCING AN ENDOSCOPE THROUGH A BODY PASSAGE

BACKGROUND AND SUMMARY

The use of a flexible endoscope (fiberscope) for examining the interior wall of a body passage such as the colon is well known. Flexible fiberoptic colonoscopy plays an important role in the preoperative and postoperative diagnostic evaluation of the condition of the large bowel for cancer, it being recognized that carcinoma of the colon stands as the second most common cause of cancer deaths. Although instrumentation necessary for examination of the entire colon is available, the use of such equipment presently requires the services of a highly skilled colonoscopist, in contrast to those of a general endoscopist, if the risks of perforating the colon and life-threatening hemorrhaging are to be kept low. Even experienced examiners are known to fail in trying to reach and examine the entire colon because of anatomical variations and pathological alterations. Persistence in trying to overcome such obstacles can lead to complications even when the procedure is carried out by an experienced colonoscopist.

This invention is concerned with reducing the above limitations in employment of fiberoptic colonoscopy and, in general, with decreasing the hazards and complexities associated with the use of currently-available flexible endoscopes in conducting visual diagnostic internal examination of the colon and other body passages. Another aspect of the invention lies in providing an improved endoscope equipped with means adjacent its distal end to assist in the advancement of the endoscope through a tubular body passage.

In brief, the combination includes a sleeve which extends about and is secured to the distal end portion of a flexible endoscope. The sleeve has an outer tubular wall of resilient flexible material which, in combination with the endoscope or with an inner wall in direct engagement with the endoscope, defines an expandable annular chamber. At least one conduit communicates with the chamber and with a pulsatile fluid source for supplying fluid for repetitious expansion and contraction of the chamber. The outer wall has a multiplicity of resilient hollow protrusions, each of which is movable between a partially-inverted retracted condition (when the chamber is unexpanded) and an outwardly- and rearwardly-projecting extended condition when the chamber is expanded by the pressure fluid. Direct engagement between the resilient protrusions and the wall of the body passage helps to advance the endoscope along that passage.

References illustrative of the prior art are U.S. Pat. Nos. 3,485,237, 2,855,934, 3,895,637, 2,356,659, 3,911,927, 3,168,092, 3,982,544, 3,669,099, 3,794,041 and 3,665,928.

Other advantages, features, and objects of the invention will become apparent from the specification and drawings.

DRAWINGS

FIG. 1 is a perspective view of a device embodying the present invention.

FIG. 2 is an enlarged cross sectional view taken along line 2—2 of FIG. 1.

FIG. 3 is a side elevational view illustrating the device in combination with a conventional endoscope.

FIG. 4 is an enlarged longitudinal sectional view illustrating one of the resilient protrusions of the device in its retracted condition.

FIG. 5 is a longitudinal sectional view similar to FIG. 4 but illustrating the resilient protrusion in its fully extended condition.

FIG. 6 is a longitudinal sectional view illustrating the construction and operation of a modified protrusion.

DETAILED DESCRIPTION

Referring to the drawings, the numeral 10 generally designates a tubular sleeve connected by conduit 11 to a pulsatile fluid source 12. In the embodiment illustrated, the sleeve is composed of inner and outer walls 13 and 14 formed of elastomeric material and defining an elongated annular chamber 15 therebetween. The inner wall 13 defines a lumen 13a which is dimensioned to receive the stem of an endoscope 16.

As shown in FIG. 3, the sleeve is positioned adjacent the distal end of the endoscope and is secured against longitudinal sliding movement along that endoscope. If desired, a suitable adhesive may be interposed between the outer surface of the endoscope stem and the inner surface 13a of the sleeve in order to prevent longitudinal movement between the parts. Alternatively, the inner wall 13 of the sleeve, when formed of elastomeric material, may have an inside diameter slightly smaller than the outside diameter of the endoscope so that the sleeve will grip the endoscope and be secured against relative longitudinal movement without the need for adhesive connection.

The tubular inner and outer walls 13 and 14 are joined together at opposite ends of the sleeve so that chamber 15 is sealed except for the passage of conduit 11 which communicates with that chamber. Source 12, shown diagrammatically in FIG. 1, may be any suitable source of pulsatile fluid such as, for example, a variable-volume chamber associated with a piston or membrane which is mechanically and cyclically shifted to cause the fluid within the variable-volume chamber to surge away from and then return to that chamber. The system may be a closed one involving the chamber 15 of the sleeve, the passage of conduit 11, and the variable-volume chamber of the pulsatile fluid source 12. In such a closed system, fluid would flow into chamber 15 of the sleeve as fluid is displaced from the variable-volume chamber of source 12 and, conversely, such fluid would be drawn from chamber 15 as the variable-volume chamber expands. While a power-operated variable-volume chamber is indicated, any of a variety of well-known devices for introducing fluid into and withdrawing fluid from chamber 15 may be utilized. The frequency of the pulsatile action should fall within the general range of 5 to 240 cycles per minute (cpm) and, preferably, approximately 60 to 180 cpm. The fluid may either be a liquid (such as water) or a gas (such as air).

The resilient outer wall 14 is formed to provide a multiplicity of hollow resilient protrusions 17 which are integral with that wall and which define cavities 18 communicating with chamber 15 (FIGS. 4 and 5). Each protrusion projects outwardly and rearwardly (or proximally) when the pressure within chamber 15 and cavity 18 is positive. When the pressure within the chamber is reduced, each protrusion retracts as depicted most clearly in FIG. 4. Movement between extended and retracted positions may be facilitated by forming each protrusion with a shank portion 17a of reduced thickness and a head portion 17b of greater thickness. In such a case, the shank portion may invert or fold inwardy upon retraction of each protrusion (FIG. 4), the extent of such infolding depending largely on the stretchability (or lack of strechability) of the material of wall 14. If desired, the wall thickness of head portion 17b may be approximately the same as the wall thickness of the cylindrical portion of outer wall 14 as revealed in FIGS. 4 and 5.

In the embodiment of FIGS. 1-5, each protrusion or finger 17 is angled rearwardly and outwardly at an angle x falling within the general range of 20 to 60 degrees. The preferred range is believed to be about 40 to 50 degrees with 45 degrees regarded as the optimum.

Endoscope 16 is a conventional flexible endoscope which is capable of transmitting an image as well as light for illumination. Such devices are ordinarily composed of a multiplicity of light-transmitting glass fibers which are bundled together in precisely oriented fashion to transmit an illuminated image from the objective or distal end 16a to the eyepiece (not shown). Other fibers alongside the bundle are utilized to transmit illuminating light to the distal end of the instrument. All of the fibers are sealed or potted within a protective sheath 16b which is ordinarily flexible but may, if desired, be relatively rigid. Since such a fiberscope is entirely conventional and is well known in the art, a more detailed description of its construction and operation is believed unnecessary herein.

In the operation of the device, the pulsating flow of fluid causes the hollow protrusions 17 to extend and retract in cyclic frequency. As the protrusions move into their extended positions at least some of them engage the inner wall of the colon or other body passage, such wall being indicated generally by line 19 in FIG. 5. The expansion of the protrusions tends to urge the endoscope forwardly in the direction indicated by arrow 20. The crawling action produced by expansion of the fingers or protrusions augments the force normally applied by the endoscopist to urge the instrument forwardly within the body passage. Should the distal end portion of the endoscope engage a sharply-curved wall of the passage which would otherwise impede advancement of the instrument or present risks of wall perforation, the gentle forces exerted by the protrusions 17 as they expand against the wall of the passage tends to relieve the binding effect and promote advancement of the scope through the passage.

The outer wall 14 of the sleeve may be formed from any suitable elastomeric material such as, for example, natural or synthetic rubber. Inner wall 13 may be formed from the same material and, in such a case, it is believed apparent that a pressure increase within chamber 15 will tend to urge wall 13 radially inwardly towards the outer surface of the endoscope (as represented by numeral 21 in FIGS. 4 and 5). Consequently, when the sleeve is frictionally carried by the distal end portion of the endoscope, the increase in pressure within chamber 15 not only serves to extend protrusions 17 but also causes the resilient inner wall to grip the outer surface of the endoscope more tightly.

Inner wall 13 may instead be formed of a less pliable material than the outer wall 14 since the primary functions of the inner wall are to contribute in defining a sealed chamber 15 and to secure the sleeve to the endoscope. When removability of the sleeve is not considered necessary or desirable, wall 13 may constitute a wall portion of the endoscope itself, the outer resilient wall 14 of the sleeve thus being secured at its ends directly to the endoscope to define the expandable chamber 15.

The length of the sleeve 10, the wall thickness and dimensions of that sleeve, and the number, shape and size of the expandable protrusions may vary widely depending on the endoscopic instrument with which the sleeve is intended to be used. In the illustration given, each protrusion takes the form of a hollow finger of limited longitudinal and circumferential extent with respect to the sleeve as a whole; however, it is to be understood that the circumferential dimension of each protrusion may be increased substantially without impairing the operation described and that in some applications it may be desirable to provide protrusions of considerable circumferential extend up to a complete toroidal shape rather than a multiplicity of circumferentially-spaced fingers as shown. In any event, such protrusions should be spaced apart longitudinally throughout substantially the entire length of outer wall 14. As already described, inflation of chamber 15 not only causes extension of the protrusions 17 but also results in slight radial expansion of the annular chamber. Such radial expansion may be reduced, if desired, by joining the inner and outer walls with a plurality of longitudinally-extending radial ribs 22 represented by phantom lines in FIG. 2.

The embodiment of FIG. 6 is the same as the construction already described except for differences in the configuration of hollow protrusions 17'. By controlling the thickness or the length of material of the shank portion 17a' on the proximal side of each protrusion, in relation to the thickness or length of such material on the distal side of that protrusion, it is possible to provide a construction in which the direction of movement of the head portion 17b' of each protrusion changes with the degree of expansion or extension of that protrusion. In FIG. 6, the length of material on the rear or proximal side is substantially less than the material on the front or distal side so that, as the protrusion extends, the head portion 17b' transcribes a curved path indicated by arrow 23. At the commencement of its movement, the head portion 17b' moves in a path having a greater radial component with respect to the sleeve as a whole, and as the protrusion becomes fully expanded or extended, the direction of movement of the head portion has a greater axial component. To achieve such curvilinear movement, the shank portion 17a' may be provided with greater thickness, and hence less stretchability for a given force, on the proximal side of each protrusion, either in addition to or in lieu of the reduced length depicted in FIG. 6. By constructing each protrusion so that it extends along such a curvilinear path, the effective pushing action of each protrusion, and the crawling action of the sleeve as a whole, may be increased.

The embodiment of FIG. 6 also reveals that the head portion 17b' of each protrusion may be provided with an undulating or irregular outer surface to increase the gripping action of the fingers or protrusions as they expand into engagement with the colon or other body passage.

While in the foregoing we have disclosed embodiments of the invention in considerable detail for purposes of illustration, it will be understood by those skilled in the art that many of these details may be varied without departing from the spirit and scope of the invention.

We claim:

1. A sleeve for facilitating the advancement of an endoscope through a tubular body passage, said sleeve having inner and outer tubular walls of resilient flexible material disposed in coaxial relation and joined together at their opposite ends to define a chamber therebetween, said inner tubular wall defining a lumen adapted to receive a portion of an endoscope and said outer wall having a multiplicity of resilient hollow protrusions disposed thereabout, said protrusions extending rearwardly as well as outwardly from said sleeve when said sleeve is expanded by fluid within said chamber and collapsing generally radially inwardly into retracted condition when said fluid within said chamber is reduced, and conduit means communicating with said chamber for conveying fluid to and from said sleeve for extending and retracting said protrusions.

2. The sleeve of claim 1 in which said protrusions are disposed in spaced relation along substantially the full length of said sleeve.

3. The sleeve of claim 1 in which said protrusions are formed integrally with said outer wall.

4. The sleeve of claim 3 in which each of said hollow protrusions has a head portion and a shank portion, said shank portion having a wall thickness less than the thickness of the outer wall of said sleeve extending thereabout.

5. The sleeve of claim 4 in which said shank portion also has a wall thickness less than that of said head portion.

6. The combination of claim 5 in which said shank portion has a wall thickness which is thicker on the rear side of each protrusion than on the forward side thereof.

7. The combination of claim 5 in which said shank portion of each protrusion is shorter on the rear side of each protrusion than on the forward side thereof.

8. The sleeve of claim 1 in which each said protrusion when extended projects outwardly and rearwardly at an angle with respect to the axis of said sleeve within the range of about 20 to 60 degrees.

9. The sleeve of claim 8 wherein said range falls within about 40 to 50 degrees.

10. The sleeve of claim 1 in which said conduit also communicates with a fluid source including means for pulsating said fluid to cause said protrusions to cyclically extend and retract.

11. The sleeve of claim 1 in which an endoscope has a distal end portion extending through the lumen of the inner wall of said sleeve.

12. The sleeve of claim 11 in which said inner wall is formed of elastomeric material, said lumen being smaller in cross sectional dimensions than said distal end portion of said endoscope when said inner wall is in unstretched condition.

13. In combination with an endoscope having a distal end portion for insertion into and advancement within a body passage, a sleeve for facilitating such advancement, said sleeve comprising an outer tubular wall of elastomeric material extending about said distal end portion and being secured to said end portion to provide an annular chamber therebetween, conduit means communicating with said chamber for conducting fluid to and from said chamber, and a pulsatile fluid source connected to said conduit for supplying fluid under pulsating pressure to said conduit and chamber, said outer wall having a multiplicity of resilient hollow protrusions formed therein, each of said protrusions being movable between an outwardly- and rearwardly-projecting extended condition when said chamber is expanded by said fluid and a partially-inverted and generally radially inwardly retracted condition when fluid is withdrawn from said chamber.

14. The combination of claim 13 in which said protrusions are disposed in spaced relation along substantially the full length of said sleeve.

15. The combination of claim 13 in which said protrusions are formed integrally with said outer wall.

16. The combination of claim 15 in which each of said hollow protrusions has a head portion and a shank portion, said shank portion having a wall thickness less than the thickness of said outer wall extending thereabout.

17. The combination of claim 16 in which said shank portion also has a wall thickness less than that of said head portion.

18. The combination of claim 17 in which said shank portion has a wall thickness which is thicker on the rear side of each protrusion than on the forward side thereof.

19. The combination of claim 17 in which said shank portion of each protrusion is shorter on the rear side of each protrusion than on the forward side thereof.

20. The combination of claim 13 in which said sleeve also includes an inner tubular wall disposed internal to said outer wall and external to said distal end portion of said endoscope, said inner wall being sealed at its ends to said outer wall to define said annular chamber.

21. The combination of claim 20 in which said inner wall is secured to said endoscope.

22. The combination of claim 13 in which each said protrusion when extended projects outwardly and rearwardly at an angle within the range of about 20 to 60 degrees with respect to the axis of said endoscope.

23. The combination of claim 22 in which said range is about 40 to 50 degrees.

24. A method for facilitating the advancement of an endoscope through a tubular body passage, comprising the steps of enclosing a distal portion of said endoscope in a sleeve of elastomeric material having a multiplicity of resilient protrusions formed therein, and cyclically introducing fluid into said protrusions to cause the same to expand radially outwardly and rearwardly into contact with said body passage and then withdrawing fluid from said protrusions to retract the same into said sleeve.

25. The method of claim 24 in which said endoscope is independently and simultaneously urged axially forwardly within said passage as said protrusions are cyclically extended and retracted.

* * * * *